United States Patent
Osman-Ponchet

(10) Patent No.: US 9,400,283 B2
(45) Date of Patent: Jul. 26, 2016

(54) IN VITRO METHOD USING HUMAN SKIN FOR EVALUATING THE INFLUENCE OF ABC TRANSPORTERS

(75) Inventor: Hanan Osman-Ponchet, Antibes (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 14/130,268

(22) PCT Filed: Jun. 27, 2012

(86) PCT No.: PCT/FR2012/051476
§ 371 (c)(1),
(2), (4) Date: Dec. 30, 2013

(87) PCT Pub. No.: WO2013/001232
PCT Pub. Date: Jan. 3, 2013

(65) Prior Publication Data
US 2014/0162291 A1    Jun. 12, 2014

Related U.S. Application Data

(60) Provisional application No. 61/503,061, filed on Jun. 30, 2011.

(30) Foreign Application Priority Data

Jul. 29, 2011    (FR) ...................................... 11 56939

(51) Int. Cl.
G01N 33/53    (2006.01)
G01N 33/68    (2006.01)
G01N 33/566    (2006.01)

(52) U.S. Cl.
CPC .......... *G01N 33/6881* (2013.01); *G01N 33/566* (2013.01); *G01N 33/68* (2013.01)

(58) Field of Classification Search
None
See application file for complete search history.

(56) References Cited

PUBLICATIONS

Sougrat et al. (2002) J. Invet. Dermatol. 118: 678-685.*
Ito, K. et al., "P-Glycoprotein (Abcb1) is involved in absorptive drug transport in skin," Journal of Controlled Release, Elsevier, Amsterdam, NL, vol. 131, No. 3, Nov. 2008, pp. 198-204.
Ito, K. et al., "Involvement of organic anion transport system in transdermal absorption of flurbiprofen," Journal of Controlled Release, Elsevier, Amsterdam, NL, vol. 124, No. 1-2, Nov. 2007, pp. 60-68.
Szakacs, G., et al., "The role of ABC transporters in drug absorption, distribution, metabolism, excretion and toxicity (ADME-Tox)," Drug Discovery Today, Elsevier, Rahway, NJ, vol. 13, No. 9-10, May 2008, pp. 379-393.
Baron, J. M., et al., "Expression of Multiple Cytochrome P450 Enzymes and Multidrug Resistance-Associated Transport Proteins in Human Skin Keratinocytes," Journal of Investigative Dermatology, vol. 116, No. 4, Apr. 2001, pp. 541-548.
Ernst, I. M., et al., "Cellular uptake, stability, visualization by Naturstoff reagent A, and multidrug resistance protein 1 gene-regulatory activity of cyanidin in human keratinocytes," Pharmacological Research, Academic Press, London, GB, vol. 61, No. 3,. Mar. 2010, pp. 253-258.
Scherrmann, Jean-Michel, "Transporters in Absorption, Distribution, and Elimination," Chemistry & Biodiversity, vol. 6, No. 11, Nov. 2009, p. 1933-1942.

* cited by examiner

*Primary Examiner* — Michael Pak
(74) *Attorney, Agent, or Firm* — Dentons US LLP

(57) ABSTRACT

An in vitro method is described that uses full-thickness human skin for evaluating the influence of ABC transporters (such as MDR1, MRP1, MRP2 or BCRP) on the absorption and distribution of topically applied medicinal substances.

8 Claims, 15 Drawing Sheets

Radiolabel

Intact skin          Stripped skin

IN VITRO METHOD USING HUMAN SKIN FOR EVALUATING THE INFLUENCE OF ABC TRANSPORTERS

CROSS-REFERENCE TO PRIOR APPLICATIONS

This application is a National Stage of PCT/FR2012/051476, filed Jun. 27, 2012, and designating the United States (published in English on Jan. 3, 2012, as WO 2013/001232 A1), which claims priority under 35 U.S.C. §119 to U.S. Provisional Patent Application 61/503,061, filed Jun. 30, 2011, each hereby expressly incorporated by reference in its entirety and each assigned to the assignee hereof.

In vitro method using full-thickness human skin for evaluating the influence of ABC transporters (such as MDR1, MRP1, MRP2 or BCRP) on absorption and distribution of topically applied drugs is described.

BACKGROUND

ATP Binding Cassette (ABC) transporters are a family of integral membrane proteins present in all cells of all species of archaea, eubacteria and eukaryota. Methods for evaluating the influence of ABC transporters (such as MDR1, MRP1, MRP2 and/or BCRP) on absorption and distribution of topically applied drugs have been described, but are not optimal.

SUMMARY

Exemplary embodiments provide an in vitro method using human skin for evaluating the influence of skin ABC transporters on absorption and distribution of topically applied drugs.

The method generally includes the followings steps:
(1) Preparing ex vivo human skin samples, and maintaining skin samples in organoculture conditions,
(2) Contacting a first skin sample with a specific ABC transporter inhibitor solubilized in a vehicle in organoculture conditions,
(3) Contacting a second skin sample (control) with the vehicle in organoculture conditions,
(4) Contacting both control and ABC transporter inhibitor treated skin samples with a drug in organoculture conditions,
(5) Determining for each skin sample the amount of drug collected in the liquid receptor (absorption) after penetration through the skin,
(6) Determining for each skin sample the amount of drug located in the skin samples (distribution),
(7) Comparing the level of uptake of the drug in the first skin sample (with inhibitor) with that of the control skin sample (without inhibitor).

The vast majority of ABC transporter proteins control the transport across cellular membranes of molecules ranging from small ions to drugs, lipids and proteins. The human genome encodes 48 ABC transporter genes.

Most of the 48 human ABC transporters play a role in the export of physiological substrates (amino acids, peptides, lipids, inorganic ions . . . ), and among them, nine are associated to a Multi-Drug Resistance (MDR) phenotype, due to their ability to extrude out of the cells a large variety of xenobiotics. These are the P-glycoprotein (ABCB1, P-gp or MDR1), the Multidrug Resistance associated Proteins or MRPs (MRP1-MRP7, also referred to as ABCC1-6 and ABCC10), and the Breast Cancer Resistance Protein or BCRP (ABCG2).

As ABC transporters, MDR1 and P-gp are in particular widely distributed in the organism [Thiebaut F, Tsuruo T, Hamada H, & al. *Cellular localization of the multidrug-resistance gene product P-glycoprotein in normal human tissues. Proc. Natl. Acad. Sci. USA* 1987; 84: 7735-8.], they also play an important role in the modulation of absorption, tissue distribution and elimination of their substrates. MDR ABC transporters are therefore considered as a major intervenient in the pharmacokinetics of many drugs, which can in turn modulate their pharmacological activity or their toxicity.

Based on these properties and from a cellular point of view, ABC transporter transfers drugs extracellularly by coupling with them and regulates the disposition profile of drugs (drug effective concentration in absorption, distribution, metabolism, excretion, site on target), which in turn determines the total pharmacological effect of the drugs.

For example, ABC transporter, which is expressed in intestinal epithelial cells and cerebrovascular endothelial cells, has a great influence on the bioavailability of orally administered drugs and drug migration to the central nervous system.

As another example, when P-glycoprotein and MRP1 are overexpressed, it is well known in the field of chemical therapy of cancer that cancerous cells become tolerant by excreting many anti-cancerous drugs out of the cells.

This functional role of ABC transporters can apply when drugs are administered by the oral or enteral route. But, in the case of dermatological products wherein drugs are applied topically, little is known about the functional role of transport proteins which are constitutively expressed in the skin and specifically in the human skin.

Multidrug Resistance associated Proteins or MRPs have been reported to be expressed in normal human epidermal keratinocytes (NHEKs), also its function is unclear [Baron J M, Holler D, Schiffer R & al. *J Invest Dermatol,* 2001; 116; 541-548.], and MRP1 was the most highly expressed of the drug transporter genes analysed by real time PCR in human skin [Smith G, Dawe R S &al. *J Invest Dermatol,* 2003; 121; 390-398].

More recently, using the same real-time PCR analysis, MDR1 mRNA expression was demonstrated to be up to 360-fold higher in whole human skin specimens in comparison with expression in NHEKs. Strong expression of MDR1 mRNA was especially detected in human dermis (‡300-fold higher than in NHEKs), whereas epidermal mRNA expression was only slightly higher (12-fold) than expression in NHEK [Shazik C, Wenzel J & al, *Experimental Dermatology,* 2011; 1-3]. In fact, ABC transporters would function in a viable skin layer (viable epidermis and dermis), but not in stratum corneum that consists of dead cells.

On another side, using immunohistochemistry, a strong expression of P-gp protein was revealed in different compartments of human skin such as sweat ducts, vessels, nervesheaths and muscles of human skin. Only moderate expression of P-gp protein was seen in the basal epidermis layer [Shazik C, Wenzel J & al, *Experimental Dermatology,* 2011; 1-3].

Another study showed the involvement of the MDR1 or P-gp transporter in the cutaneous absorption of medicinal substances [Ito K, et al., J. Control Release, 2008, 198-204]. In this study, the authors used mouse skin which does not express the gene coding for MDR1 and an in vitro process which is adapted to measuring the intestinal absorption (Ussing chamber) rather than the cutaneous absorption. In this process, both sides of the skin sample are placed in contact with a liquid medium in which is dissolved the test substance. It is thus a model that is very remote from topical application in which only the dermal part is in contact with the liquid, while the epidermis is left in the open air. In this study, the authors compared the absorption of rhodamine 123 (MDR1 substrate) in wild-type mouse skin and mouse skin which does not express the MDR1 gene. The absorption of rhodamine in the epidermis-dermis direction (absorption) was greater in the wild-type mouse skin than in the mouse skin not expressing the MDR1 transporter, which led the authors to conclude that the MDR1 transporter plays a role in the cutaneous absorption of medicinal substances.

Although the process used by the authors (Ussing chamber) may be contestable since it is not adapted to topical application, the use of genetically modified mouse skin made it possible to demonstrate the role of P-gp in cutaneous absorption in mice. However, the involvement of P-gp in cutaneous absorption on human skin cannot be demonstrated, and furthermore the model used cannot be used for studying the role of other ABC transporters such as MRP1 in the cutaneous absorption of the medicinal substances used by topical application, unless other animals are genetically modified.

Thus, in light of knowledge that certain ABC transporters such as MDR1 or the P-gp protein have broad substrate specificity, their expression in different compartments of the human skin can be an important consideration for drug development, especially for topical dermatological drugs.

Indeed, there is a need to have a method to evaluate directly on human skin the influence of ABC transporters on the penetration of drugs applied topically.

Such a method applied to human skin is needed to better understand the role of transporters in the disposition of currently available topical drugs, as well as to develop the capability of predicting the contribution of ABC transporters in the disposition of new molecular entities under development.

The need to develop a method directly applicable on human skin appears to be more essential knowing that differences in substrate recognition and transport activity exist between animal (such as mouse) and human orthologous transporters (such as MRP1 for example), indicating that significant interspecies differences, exist [Stride BD & al in *Mol. Pharmacol.* 1997 September; 52(3):344-53].

DETAILED DESCRIPTION

Figure 1:
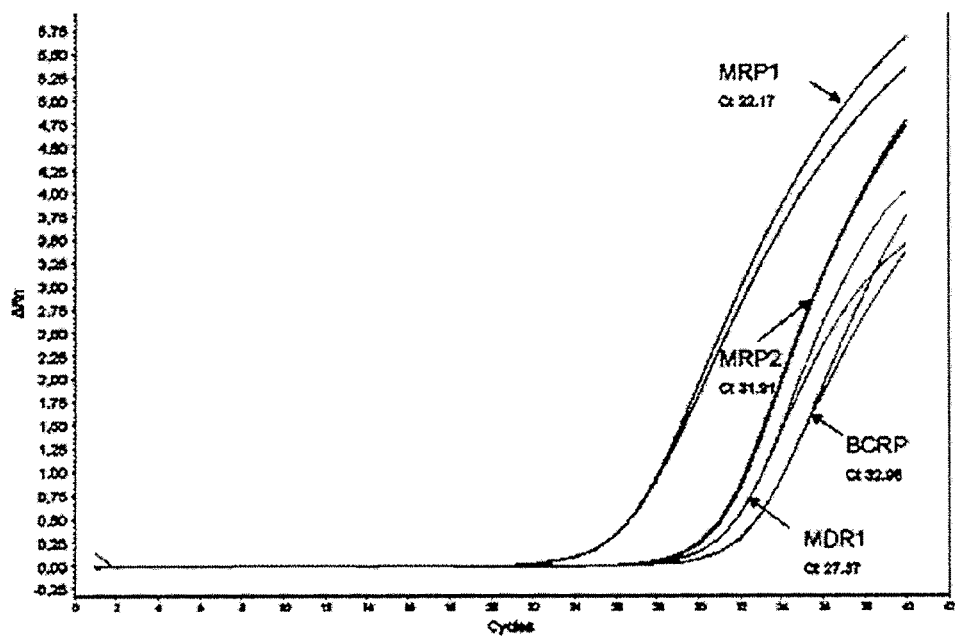
FIG. 1: Amplification curve of ABCB1, ABCC1, ABCC2 and ABCG2 in ex vivo human skin maintained in organoculture for 72 hours.

In one aspect, an exemplary embodiment provides an in vitro method using full-thickness human skin for evaluating the influence of skin ABC transporters such as MDR1, MRP1, MRP2 and/or BCRP on absorption and distribution of topically applied drugs.

The method generally includes the followings steps:
(1) Preparing full-thickness ex vivo human skin samples without subcutaneous fat, and maintaining skin samples in organoculture conditions, preferably at 37° C. during a period of time ranging from 1 min. to 72 hours,
(2) Contacting a first skin sample with specific ABC transporter inhibitor solubilized in a vehicle in organoculture conditions, preferably during a period of time ranging from 1 minute to 1 hour,
(3) Contacting a second skin sample (control) with the vehicle in organoculture conditions, preferably during the same period of time as in step (2),
(4) Contacting both control and ABC transporter inhibitor treated skin samples with a drug in organoculture conditions, preferably for a period of time ranging from 1 hour to 72 hours, and more preferably around 16 hours,
(5) Determining for each skin sample the amount of drug collected in the receptor fluid (absorption) after penetration through the skin,
(6) Determining for each skin sample the amount of drug located in the skin samples (distribution),
(7) Comparing the level of uptake of the drug in the first skin sample (with inhibitor) with that of the control skin sample (without inhibitor).

For the preparation of full-thickness ex vivo human skin samples, the skin is obtained from plastic surgery. Skin samples originate from male as well as from female. They can be obtained from abdominal or mammary tissues, but also from other anatomical sites of the body.

Fresh or frozen skin samples may be used. Preferably fresh skin samples are used as the activity of ABC transporters and other enzymes is better preserved. By fresh skin samples, we understand skin samples obtained just after skin excision up to about 24 hours following excision, preferably about 4 hours after excision.

Alternatively, skin samples may be maintained in organoculture conditions up to about 72 hours after excision and before the evaluation method of ABC transporter implication starts.

Healthy skin as well as lesional skin samples are used. The subcutaneous fat of the skin is carefully removed by dissection before using it in the method.

Full thickness skin samples can be used without any treatment of Stratum Corneum, the outermost layer of skin, which acts as impermeable barrier to hydrophilic or high molecular weight drugs.

Alternatively, skin samples can be used after reducing or disrupting Stratum Corneum in order to overcome the barrier properties of this layer and to increase the penetration of the drug.

Two different approaches are used to reduce or disrupt the barrier function of the Stratum Corneum: stripping or Dermaroller®.

For the first step (1) of the method, after excision of the human skin sample and removing of the subcutaneous fat, pieces of skin (2×2 cm or less) are sectioned and are placed dermal side down in a Transwell® insert nested inside the well of a multiwell culture plate. The support on which human skin samples are placed is a permeable support with microporous membranes. Preferably, the membrane used is a polycarbonate material, but other membrane materials can be used. Such supports are sold by Corning under the name Transwell®, but other similar commercially available devices can be used in this step. The insert Transwell® used can be adapted to a 6-well, 12-well or 24-well plate. The wells are prefilled with an appropriate volume of skin long term culture medium.

Depending on the culture plate used, the volume of the medium ranges from 2.0 mL to 0.2 mL. A cylinder, preferentially manufactured in glass, but which can also be manufactured in another appropriate material, is placed on the top of the skin sample in order to delimitate the area of the skin sample to be treated. Thus, the area to be treated depends of the size of the cylinder used, which in turn is adapted to the size of the insert used. The skin surface to be treated ranges from about 0.125 $cm^2$ up to about 3 $cm^2$.

At this stage, the Transwell® plate is placed on an orbital shaker and maintained in organoculture conditions. By organoculture conditions, we understand culture temperature ranging from about 32° C. up to about 38° C., preferably about 37° C., with $CO_2$ concentration ranging from about 4% up to about 10%, preferably about 5%, and with saturated hygrometry in a cell culture incubator.

Alternatively, diffusion cells like Franz diffusion cells can also be used instead of the model described above. In this case, preferred conditions used are as follows:

Skin sections are mounted on glass diffusion cells with nominal surface areas of about 1 or about 2 $cm^2$ and receiver compartments with 3 mL capacities. The epidermal side of the skin is exposed to ambient conditions while the dermal side is bathed by a skin long term culture medium. Culture medium is kept between about 30° C. and about 38° C., preferably at about 32° C. by a water jacket controlled by a water bath. Constant stirring of the receptor fluid is maintained by magnetic stirring at about 500 rpm. Care is taken to remove all air bubbles between the under surface of the skin (dermis) and the culture medium in the receiver compartment.

Alternatively, when overcoming of Stratum Corneum is needed, two different approaches are used: stripping or perforation by Dermaroller®.

In case of stripping, skin pieces, prepared as described above, are placed onto filter paper and supported by cork plates. In order to avoid shrink of the full-thickness skin, skin samples are stretched to about their original size and fixed with pins. The surface of the skin is stripped with 5 to 50 successive pieces of adhesive tape, preferably 30 pieces of adhesive tape. The adhesive tape is of sufficient size to cover the full area of the skin which will be in contact with the test compound.

In case of perforation by Dermaroller®, skin pieces are placed onto filter paper and supported by cork plates. In order to avoid shrink of the full-thickness skin, skin samples are stretched to about their original size and fixed with pins. The Dermaroller®, for example CIT8 model with 500 μm needle lengths, is rolled with applying pressure with the hand in four directions over skin surface.

In the second step (2) of the method, a specific inhibitor of an ABC transporter solubilized in a vehicle is applied on the surface of the first skin sample. Several inhibitors can be used depending on the ABC transporters studied. Examples of ABC transporter inhibitors are presented in table 1, but are not restricted to the list.

TABLE 1

Example of ABC transporter inhibitors:

| Gene | Aliases | Inhibitor |
| --- | --- | --- |
| ABCB1 | P-gp, MDR1 | Ritonavir, Cyclosporine, Verapamil, Erythromycin, Ketoconazole, Itraconazole, Quinidine, Elacridar (GF120918) LY335979 Valspodar (PSC833) |
| ABCC1 | MRP1 | Probenecid Cyclosporine MK571 |
| ABCC2 | MRP2, cMOAT | Cyclosporine Probenecid |
| ABCG2 | BCRP, MXR | Oestrone, 17β-oestradiol, Fumitremorgin C Elacridar (GF120918), Gefitinib |

For example, a solution of Verapamil, a specific inhibitor of ABCB1 (P-gp or MDR1), is prepared at a final concentration of 10 mM in a vehicle consisting, for example, of ethanol/NaCl about 0.9% (25/75, v/v).

Skin samples are treated with about 10 μL/$cm^2$ of about 10 mM Verapamil solution during about 30 minutes. In the case where Transwell inserts are used, the incubations are preferably conducted at about 37° C. in 5% $CO_2$ on an orbital shaker in a humidified incubator for about 30 minutes.

In the third step (3) of the method, the vehicle only is applied on the surface of the second skin sample (control). Parallel to the treatment with the inhibitor, different skin samples (same treatment of skin surface, intact, stripped or dermarolled) are treated with about 10 μL/$cm^2$ of the vehicle, for example consisting of ethanol/NaCl about 0.9% (25/75, v/v), during about 30 minutes. These samples are used as control samples without inhibitor.

In the fourth step (4) of the method, a drug is both applied on the first skin sample (with inhibitor) and on the second (control) skin samples (without inhibitor).

The drug which is used to evaluate the implication of ABC transporters in its cutaneous absorption and distribution may be a fluorescent compound, a radiolabeled compound or an unlabeled compound. This drug is used at an appropriate concentration, generally ranging from about 0.01 mM to about 100 mM in an appropriate vehicle depending on the characteristics of the drug tested.

At the end of treatment period with the inhibitor or with the vehicle, the skin samples are treated with a defined volume/amount of the drug for a period of time ranging preferably from about 1 hour to about 72 hours, and more preferably around about 16 hours.

In the fifth step (5) of the method, after incubation for the period of time predetermined in step (4), the receptor fluid is collected, immediately analyzed or stored at appropriate temperature (between +4° C. and −80° C.) before being analyzed. The amount of drug that reached the receptor fluid (absorption) is then determined with the appropriate analysis apparatus. For example, HPLC with UV, fluorescence, radioactive or mass spectrometry detection may be used to measure the amount of the drug in the receptor fluid.

In the case of radiolabeled drug, the radioactivity in the receptor fluid is analyzed by liquid scintillation counting.

In the case of a fluorescent drug, the intensity of fluorescence in the receptor fluid is directly measured with a microplate spectrofluorometer.

In some cases, the receptor fluid can be directly analyzed without any extraction procedure.

In other cases, an extraction step can be done before analyzing the receptor fluid.

In the sixth step (6) of the method, after incubation for the period of time predetermined in step (4), the amount of drug distributed in the skin (distribution) is determined. The excess of the drug is removed by wiping the skin with five cotton buds impregnated with appropriate solvent. In some cases, stripping of skin samples may be performed using 6 tape stripes. The skin samples are frozen at about −80° C. before analysis.

For determination of the drug amount in the different skin layers (distribution), frozen skin samples are cut into small pieces, fixed on a pre-cooled microtome sample holder. The skin is cut perpendicular to the surface into about 5 to about 10 μm thick sections using a cryomicrotome. In some cases, sections parallel to skin surface may be performed.

Skin sections cut perpendicular to skin surface are analyzed by autoradiography or microautoradiography in the case of radiolabeled drug, or by confocal or epi-fluorescece microscopy in the case of fluorescent drug.

Skin sections cut parallel to skin surface are analyzed by liquid scintillation counting in the case of radiolabeled drug or by HPLC with an appropriate detection mode after extraction of the drug from skin sections.

In the seventh step (7) of the method, a comparison of the level of uptake of the drug in the first skin sample (with inhibitor) is made with that of the control skin sample (without inhibitor). The amount of the drug that reached the receptor fluid (absorption) in skin samples treated with both ABC transporter inhibitor and the drug is compared with that in skin samples only treated with the drug. If lowest amount of drug is observed in skin samples treated with the ABC transporter inhibitor, this indicates that ABC transporter is implied in the skin absorption of the drug. If no difference is observed between both conditions (with and without inhibitors), this indicates that skin absorption is not related to the ABC transporters.

This method allows a better selection of the topically applied drugs in function of both ABC transporter affinity and the location of the site of action targeted which depends of the pathology to be treated.

Topically applied drugs are generally used in the treatment of skin diseases. However, topically applied drugs can be also used in the treatment of other unrelated skin disorders where systemic route could not be used. In certain cases, systemic treatments are used in the treatment of skin diseases.

There are 5 common types of skin diseases:

Inflammatory Skin Diseases

These include eczema, dermatitis, psoriasis, diaper rash and acne. Some of these skin diseases can last for extended periods of time. Topical ointments are usually prescribed to lessen the itching and swelling.

Viral Skin Diseases

These include chicken pox, measles, herpes 1, herpes 2, and shingles. Topical prescription medications are available for viral skin diseases.

Fungal Skin Diseases

Microscopic fungi are the cause of fungal infections. *Candida*, athlete's foot and ringworm are all viral infections. Treatments can include oral medications, topical ointments, powders, and oral antiseptics.

Bacterial Skin Diseases

These include impetigo, cellulitis, MRSA, folliculitis, scabies, and necrotizing fasciitis and are all bacterial skin diseases. Treatment may involve antibiotics in order to drain the area, or in extreme cases, removing the infected area.

Cancerous Skin Diseases

Basal cell cancer, squamous cell cancer, and melanoma are types of cancerous skin diseases. Skin lesions or moles that change shape or color are signs of skin cancer.

Examples of topically applied drugs used for the treatment of skin diseases are listed below:

Acne:

Tretinoin, benzoyl peroxide, clindamycin, doxycycline, isotretinoin, tetracycline, minocycline, salicylic acid, azelaic acid, erythromycin topical, drospirenone-ethinyl estradiol, tazarotene, benzoyl peroxide-clindamycin, ethinyl estradiol-norgestimate, sulfacetamide sodium, or clindamycin-tretinoin.

Psoriasis:

Cortisone, retinoids derived from vitamin A, vitamin D analogues, salicylic and lactic acid.

Rosacea:

Metronidazole and azelaic acid.

Vitiligo:

Hydroquinone

Impetigo:

Erythromycin and mupirocin.

The following examples are provided merely as illustrative of various aspects of the invention and shall not be construed to limit the invention in any way:

EXAMPLE 1

Expression of ABC Transporters in Human Skin Samples

Human skin samples obtained from abdominal plastic surgery were maintained in organoculture during 72 hours. Two skin biopsies 6 mm in diameter were cultured in 500 μL skin long term culture medium in wells of a 24-well plate at 37° C., 5% $CO_2$ and saturated hygrometry. The culture medium was changed every 24 hours. After 72 hours culture, the 2 biopsies were ground using a Presselys 24 instrument (Ozyme) in 350 μL lysis buffer (Promega). Total RNA was then extracted using SV Total RNA Isolation System kit according to the instructions provided by the constructor (Promega). A reverse transcription reaction was then performed in a total volume of 20 μL using High capacity RNA to cDNA Master Mix provided by Applied Biosystem.

The expression of the ABCB1, ABCC2, ABCC1 and ABCG2 genes was analyzed in duplicate by real time PCR using specific sense and antisense primers and a specific TaqMan probe provided by Applid Biosystem. The GAPDH gene was used as housekeeping gene to normalize the expression of each gene.

In parallel, the expression of the four genes ABCB1, ABCC1, ABCC2 and ABCG2 was analyzed according to the same process described above in fresh human hepatocytes maintained in primary culture for 96 hours.

Figure 2:
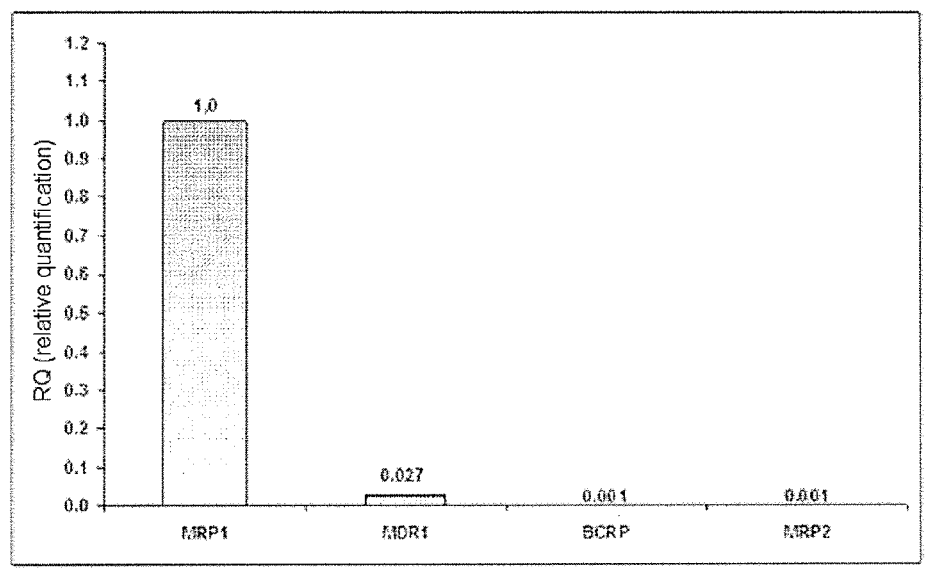
FIG. 2: Relative quantification of the expression of the ABC transporters in ex vivo human skin maintained in organoculture for 72 hours.
Figure 3:
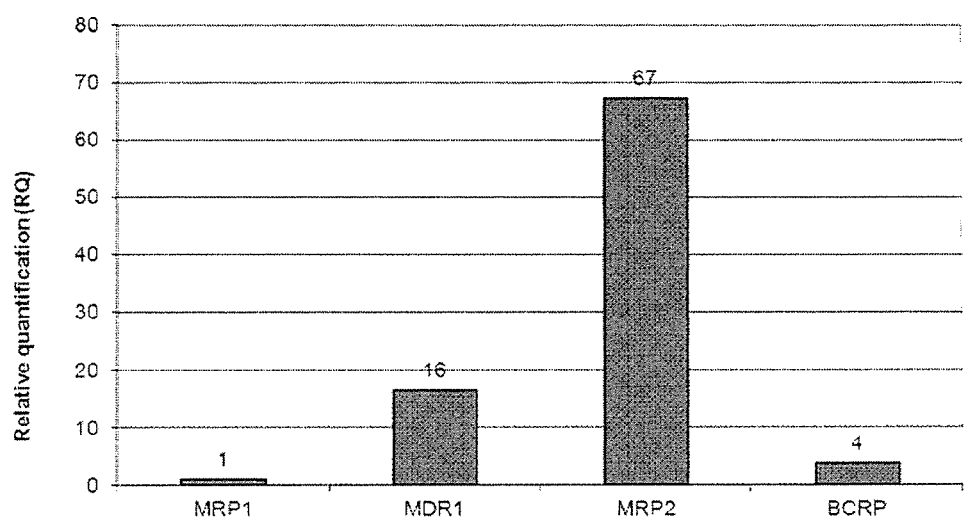
FIG. 3: Relative quantification of the expression of the ABC transporters in human hepatocytes maintained in primary culture for 96 hours.
Figure 4:
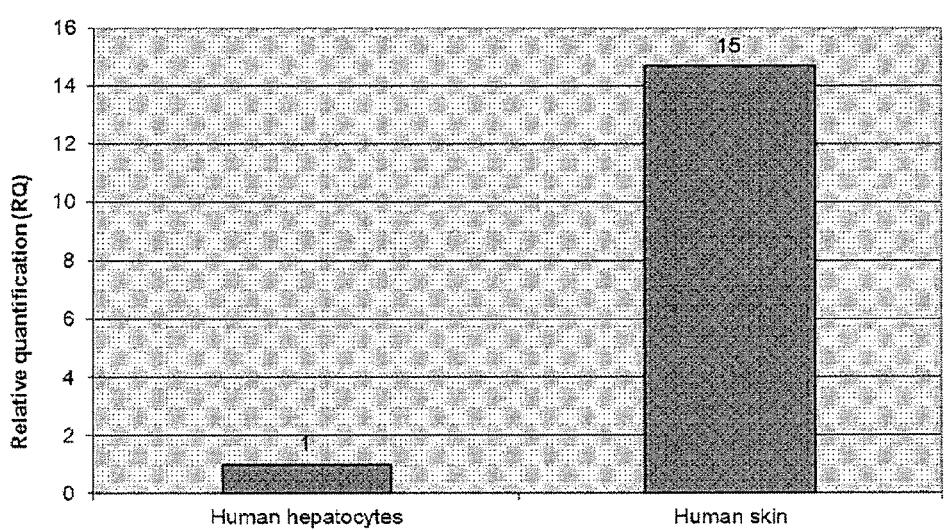
FIG. 4: Relative quantification of the expression of the ABCC1 transporter coding for MRPI in human skin organoculture and in human hepatocytes in primary culture.

FIG. 1 (Amplification curve of ABCB1, ABCC1, ABCC2 and ABCG2 in ex vivo human skin maintained in organoculture during 72 hours) shows the amplification curve of each gene amplified in human skin. FIG. 2 (Expression of the ABC transporters in ex vivo human skin maintained in organoculture during 72 hours) shows the relative expression of each gene compared to ABCC1 gene coding for MRP1 in human skin in organoculture. FIG. 3 (expression of the ABC transporters in human hepatocytes maintained in primary culture for 96 hours) shows the relative expression of each gene by comparison with the ABCC1 gene coding for MRP1 in the human hepatocytes in primary culture. FIG. 4 (expression of the ABCC1 transporter coding for MRP1 in human skin in organoculture and in human hepatocytes in primary culture) shows the relative expression of the gene coding for MRP1 in the human skin by comparison with the human hepatocytes.

The results clearly show that in ex vivo human skin maintained in organoculture during 72 hours, all the four genes are expressed in human skin. The expression of the ABCC1 gene coding for MRP1 transporter is very high compared with the genes coding for MDR1, MRP2 and BCRP for which the expression is relatively low. These results show that in human skin in organoculture, the ABC transporters are expressed, and thus human skin in organoculture can be used to study the implication of ABC transporters in the absorption and distribution of topically applied drugs.

Moreover, the results show that the expression of the genes coding for the four transporters is different in the skin and in the hepatocytes. In the hepatocytes, the expression of the three genes coding for MDR1, MRP2 and BCRP is very high by comparison with the human skin. Furthermore, in the human hepatocytes, the expression of the gene coding for MRP2 is the highest when compared with the other genes, whereas, in the human skin, it is the expression of the gene coding for MRP1 that is the highest. The comparison of the expression of the gene coding for MRP1 in the skin and in the hepatocytes reveals that the expression of the gene coding for MRP1 is 15 times higher in the human skin than in the hepatocytes. These results are thought to argue in favor of a substantial role of the MRP1 transporter in the cutaneous absorption of topically applied medicinal substances.

EXAMPLE 2

Measurement of Transepidermal Water Loss in Human Skin Samples

The transepidermal water loss (TEWL) was measured using a Tewameter TM 300® (Courage & Khazaka electronic GmbH, Germany) with an opened measurement chamber. The skin samples were mounted onto a glass diffusion cell (nominal surface area 1 or 2 $cm^2$ and receiver compartment with 3 mL capacities). The epidermal side of the skin was exposed to ambient conditions while the dermal side was in contact with the receptor fluid (skin long term culture medium (Biopredic, France), maintained at 32° C.). The initial TEWL was measured in triplicate (three skin samples). For perforation of the skin with the Dermaroller or for stripping of the skin, the skin samples were removed from the diffusion cells and fixed on cork plates and stripped or pierced as described above. After stripping or perforation, the skin samples were placed onto the diffusion cells again and the TEWL was measured in appropriate time intervals over 19 hours and 25 hours for dermaroller and stripping, respectively.

Figure 5:
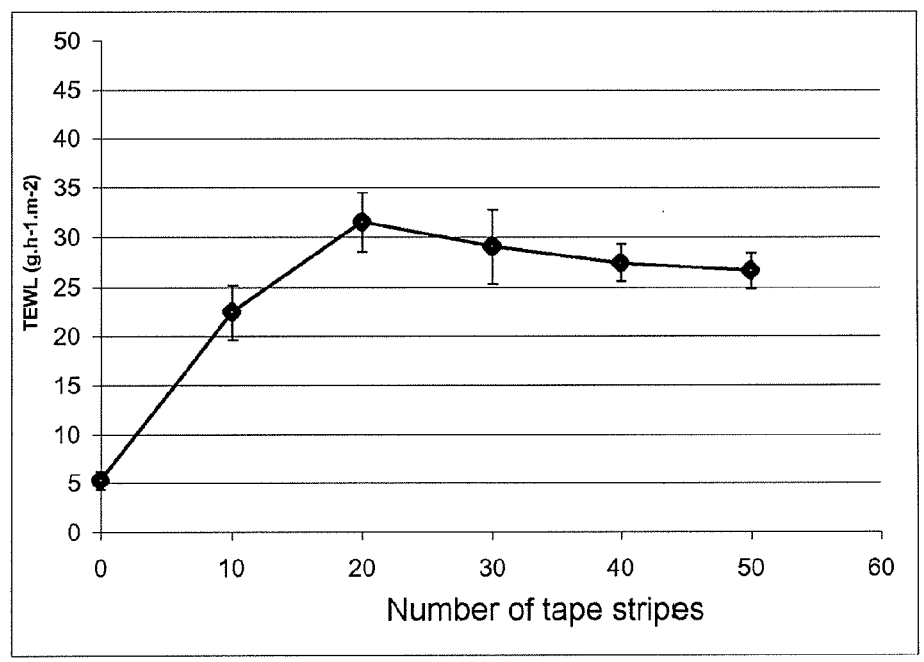
FIG. 5: Graphical representation of the effect of stripping on TEWL in ex vivo human skin samples.
Figure 6:
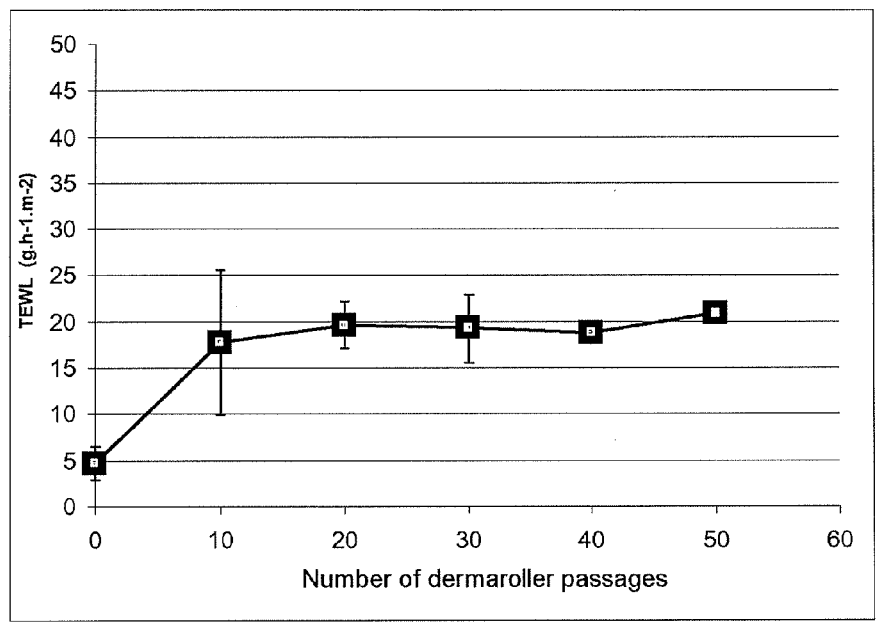
FIG. 6: Graphical representation of the effect of perforation with a dermaroller on TEWL in ex vivo human skin samples.

FIG. 5 (Effect of stripping on TEWL in ex vivo human skin samples) shows the effect of stripping on TEWL, and FIG. 6 (Effect of dermaroller on TEWL in ex vivo human skin samples) shows the effect of the dermaroller on TEWL.

The results show that TEWL value increases proportionally to the number of tape stripes used until 20 stripes, then reached a plateau. No more increase of TEWL was observed even when using 50 stripes. A six-fold increase of TEWL value was observed when using 20 tape stripes to remove the stratum corneum. The value of 30 stripes was used as standard value in the subsequent experiments.

The results also show that TEWL value increased after 20 dermaroller passages and reached a plateau with no more increase observed after 30 or 50 dermaroller passages. A four-fold increase of TEWL value was observed when using 20 dermaroller passages to disrupt the stratum corneum. The value of 32 roller passages was used as standard value in the subsequent experiments.

EXAMPLE 3

Implication of ABC Transporters in the Absorption and Distribution of Vinblastine in Human Skin Samples The model substrate molecule Vinblastine was used throughout this experiment. Vinblastine is known to be a specific substrate of MDR1.

The model inhibitor molecule Verapamil was used throughout this experiment. Verapamil is known to be a specific inhibitor of MDR1.

Tritium labeled Vinblastine was used. An isotopic solution of [$^3$H]-Vinblastine was prepared at final concentration 10 mM in methanol (1 mCi/mL).

Verapamil was prepared at final concentration of 10 mM in the vehicle consisting of ethanol/NaCl 0.9% (25/75, v/v).

Vehicle used to treat control skin samples consisted of ethanol/NaCl 0.9% (25/75, v/v).

Skin samples were first treated with the inhibitor solution verapamil. For this, 20 μL of verapamil solution was applied on the surface of skin samples using a micropipette, corresponding to 10 μL/$cm^2$ skin surface. Treatment duration with the inhibitor was 30 minutes.

In parallel, others skin samples (control samples) were treated with the vehicle of the inhibitor used, consisting of ethanol/NaCl 0.9% (25/75, v/v). For this, 20 μL of the vehicle were applied on the surface of skin samples using a micropipette. Treatment duration with the inhibitor was 30 minutes.

At the end of treatment period, both control and inhibitor treated skin samples were treated with [$^3$H]-vinblastine solution. For this, the 10 mM isotopic solution of [$^3$H]-vinblastine was diluted 4 times in 0.9% NaCl, reaching a final concentration of 2.5 mM. Twenty microliters of this diluted solution were applied on the surface of each skin sample, corresponding to 10 µL/cm². Treatment duration with vinblastine was 16 hours.

At the end of treatment duration with Vinblastine, the receptor fluid was analyzed by liquid scintillation counting in order to measure the amount of Vinblastine that reached the receptor fluid (absorption).

The distribution of Vinblastine in the skin was analyzed by autoradiography. Skin samples were placed in a tissue holder and freeze-mounted in cryomount embedding medium. The frozen blocks were sectioned into slices 8-10 µm thick, perpendicular to the epidermal surface in a cryomicrotome (Thermo Electron). The sections were collected on glass slides and dried. Cryosections were placed on a Fuji imaging plate type Bas-III (20×40 cm) in a Fujix Bas cassette 2040 during 24 hours to 5 days. The exposed plate was scanned with a Bio-Imaging analyzer (Fujix BAS 2000). The scanned images were analyzed using TINA software.

In some experiments, in vitro skin absorption of vinblastine was performed on intact skin samples without any tape stripping or dermaroller perforation. In others experiments, in vitro skin absorption of vinblastine was performed on tape-stripped skin (30 stripes) or on dermarolled (32 roller passages) skin samples.

For tape stripped skin, skin pieces with appropriate surface (about 2×2 cm) were placed onto filter paper and supported by cork plates. In order to avoid shrink of the full-thickness skin, the skin samples were stretched to about their original size and fixed with pins. The surface of the skin was stripped with 30 pieces of adhesive tape. The adhesive tape was of sufficient size to cover the full area of the skin which will be in contact with the test compound.

For perforation with dermaroller, skin pieces with appropriate surface (about 2×2 cm or less) are placed onto filter paper and supported by cork plates. In order to avoid shrink of the full-thickness skin, skin samples were stretched to about their original size and fixed with pins. The Dermaroller® CIT8 model was rolled each eight times with applying pressure with the hand in four directions over skin surface (32 passages).

The Dermaroller was provided by DISTRIMED SARL, Luxembourg. The CIT8 model was used. The CIT8 model possesses 24 circular arrays of 8 needles each of 500 µm lengths (total 192 needles) in a cylindrical assembly with 2 cm diameter and 2 cm length of the cylinder.

In vitro skin absorption of vinblastine experiments with intact and tape stripped skin samples were performed on glass diffusion cells with nominal surface area of 2 cm² and receptor fluid capacities of 3 mL. Treatment volume of skin surface was 20 µL, corresponding to 10 µL/cm². Experiments with intact skin samples were performed on 5 different donors in triplicate (N=15), whereas experiments with tape stripped skin were performed on 6 different donors in triplicate (N=18).

In vitro skin absorption of vinblastine experiments with skin samples pierced with dermaroller were performed on 6-well Transwell plate, with a treated skin area of 1 cm² and receptor fluid capacities of 1.5 mL. Treatment volume of skin surface was 10 µL corresponding to 10 µL/cm². Experiments on dermarolled skin samples were performed on 4 different donors in triplicate (N=11).

Figure 7:
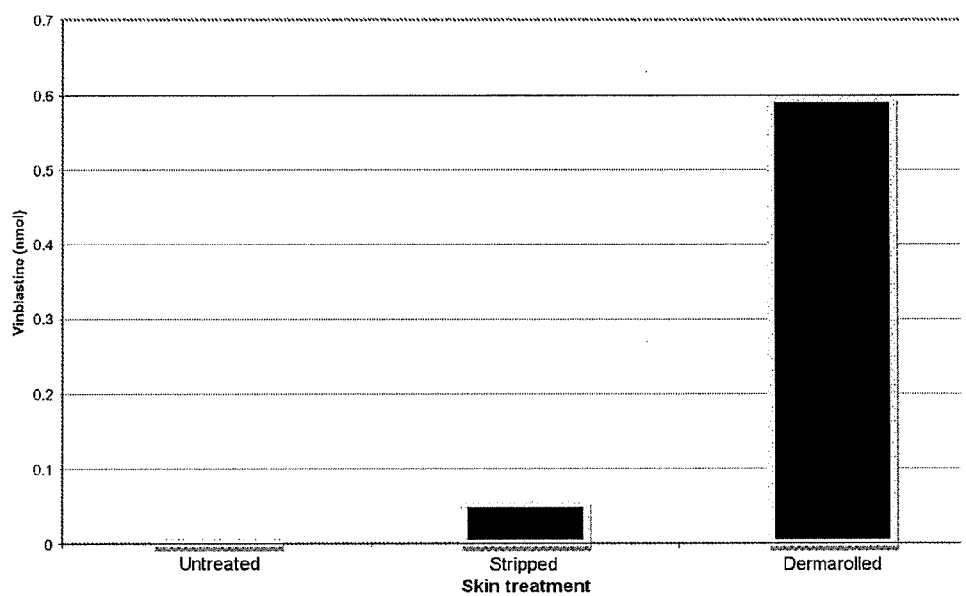
FIG. 7: Graphical comparison of skin absorption of vinblastine in intact skin, stripped skin and dermarolled skin.

FIG. 7 (Skin absorption of vinblastine in intact skin and in stripped and dermarolled skin) shows the effect of skin treatment on the human skin absorption of Vinblastine.

Figure 8:
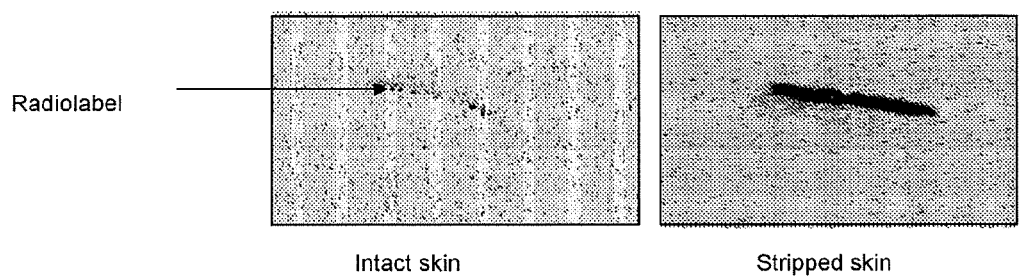
FIG. 8: Autoradiographs of skin sections comparing skin distribution of vinblastine in untreated and stripped human skin samples.

FIG. 8 (Skin distribution of vinblastine in untreated and in stripped human skin samples analyzed by autoradiography of skin sections) shows the distribution of Vinblastine in untreated and in stripped human skin analyzed by auto radiography.

Figure 9:
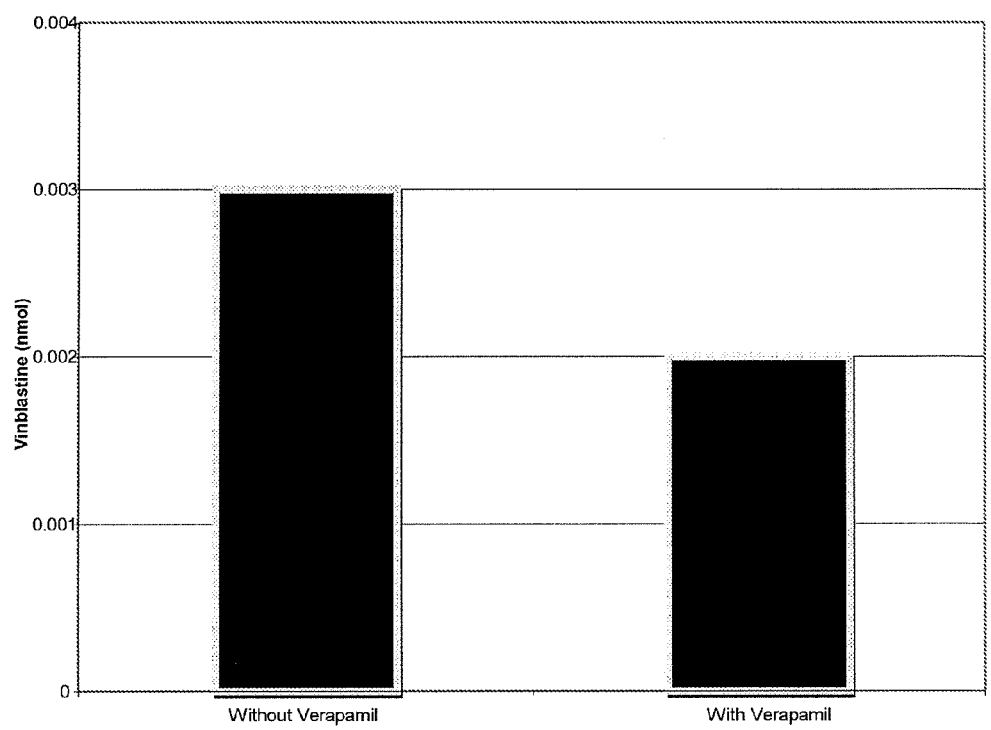
FIG. 9: Graphical comparison of vinblastine skin absorption in intact human skin samples treated with Verapamil and vinblastine skin absorption in untreated intact human skin samples.

FIG. 9 (Effect of Verapamil on Vinblastine skin absorption in intact human skin samples) shows the effect of Verapamil on Vinblastine human skin absorption in intact human skin samples.

Figure 10:
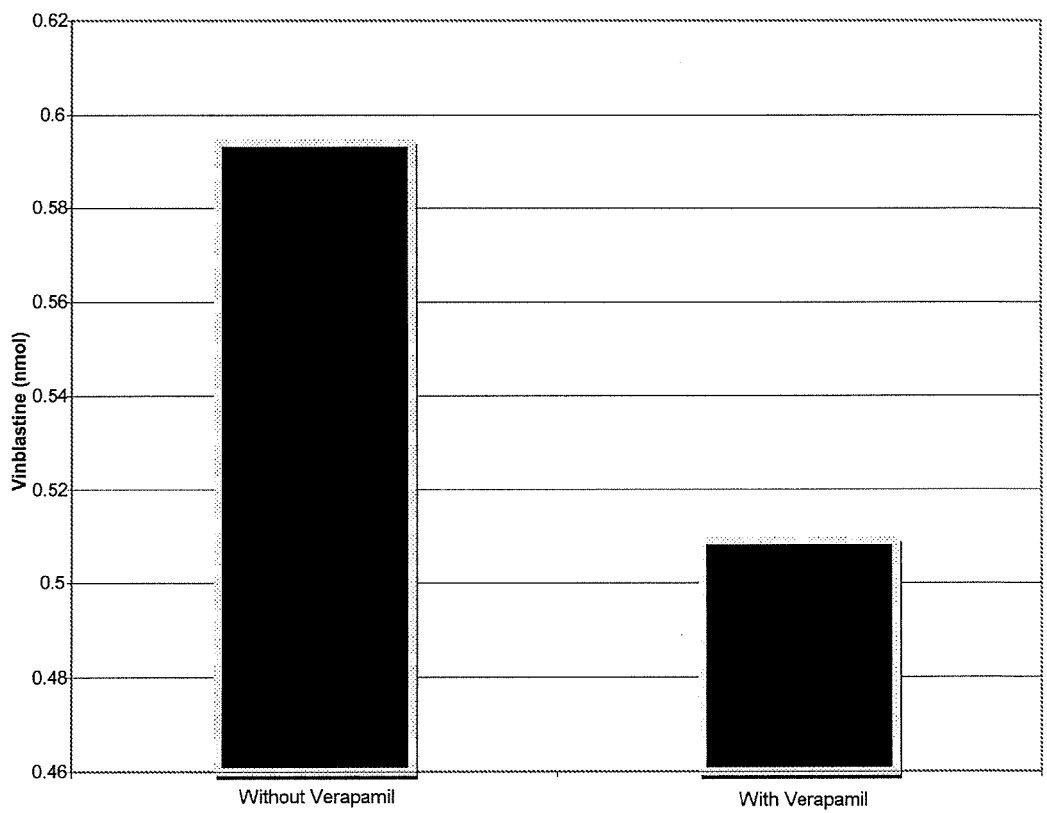
FIG. 10: Graphical comparison of vinblastine skin absorption in dermarolled human skin samples treated with Verapamil and vinblastine skin absorption in untreated dermarolled human skin samples.

FIG. 10 (Effect of verapamil on vinblastine skin absorption in dermarolled human skin samples) shows the effect of Verapamil on Vinblastine human skin absorption in dermarolled human skin samples.

The results show that in intact skin samples, vinblastine skin absorption is very low, and only representing 0.001% of the applied dose (corresponding to 0.003 nmol). Tape stripping and skin perforation with dermaroller considerably increase the skin absorption of vinblastine. Indeed, skin vinblastine absorption represented 0.07 nmol and 0.6 nmol in stripped and dermarolled skin, respectively. This implies that tape stripping increased vinblastine skin absorption by about 20 times and that skin perforation by dermaroller increased vinblastine skin absorption by about 200 times. Theses results also indicate that in the conditions used, skin perforation with dermaroller is a better tool than tape stripping for the enhancement of skin absorption of vinblastine.

The results show that in untreated skin, very weak signal related to vinblastine is observed in the topmost part of skin section corresponding to stratum corneum. No signal was observed in the deeper layers. In tape stripped skin (30 stripes) where the stratum corneum was removed, a marked increase of signal intensity related to vinblastine was observed. This indicates that tape stripping increases the penetration of vinblastine in the deeper layers of a skin sample. This result is in accordance with the result obtained in FIG. 5, showing that tape stripping increases markedly the amount of vinblastine absorbed in the receptor fluid.

The results show that in untreated skin samples, vinblastine skin absorption was reduced by verapamil treatment. Indeed, vinblastine absorption was reduced by 18% by topically applied verapamil. As verapamil is a known inhibitor of MDR1 transporter, this result suggests that MDR1 transporter is implied in skin absorption of vinblastine.

The result shows that in dermarolled human skin samples, vinblastine skin absorption was reduced by topically applied verapamil. Indeed, vinblastine skin absorption was reduced by 14% by topically applied verapamil. As verapamil is a known inhibitor of MDR1 transporter, this result suggests that MDR1 transporter is implied in skin absorption of vinblastine.

EXAMPLE 4

Implication of ABC Transporters in the Absorption and Distribution of Rhodamine 123 in Human Skin Samples The model substrate molecule Rhodamine 123 was used throughout this experiment. Rhodamine 123 is known to be a substrate of MDR1.

The model inhibitor molecule Verapamil was used throughout this experiment. Verapamil is known to be a specific inhibitor of MDR1.

Rhodamine is a fluorescent molecule. Rhodamine 123 solution was prepared at final concentration 2.5 mM in 25% DMSO.

Verapamil was prepared at final concentration of 10 mM in the vehicle consisting of ethanol/NaCl 0.9% (25/75, v/v).

Vehicle used to treat control samples consisted of ethanol/NaCl 0.9% (25/75, v/v).

Skin samples were first treated with the inhibitor solution verapamil. For this, 20 µL of verapamil solution was applied on the surface of skin samples using a micropipette, corresponding to 10 µL/cm$^2$ skin surface. Treatment duration with the inhibitor was 30 minutes.

In parallel, other skin samples (control samples) were treated with the vehicle of the inhibitor used consisting of ethanol/NaCl 0.9% (25/75, v/v). For this, 20 µL of the vehicle were applied on the surface of skin samples using a micropipette. Treatment duration with the vehicle was 30 minutes.

At the end of treatment period, both control and inhibitor treated skin samples were treated with Rhodamine 123 solution. For this, 20 µL of the 2.5 mM solution of Rhodamine 123 were applied on the surface of each skin sample, corresponding to 10 µL/cm$^2$. Treatment duration with Rhodamine 123 was 16 hours.

In vitro skin absorption of Rhodamine 123 experiments were performed with intact skin samples. Frozen skin samples were used in these experiments. After thawing, skin samples were mounted on glass diffusion cells with a nominal surface area of 2 cm$^2$ and receptor fluid capacities of 3 mL. Treatment volume of skin surface was 20 µL, corresponding to 10 µL/cm$^2$. A total of 4 different experiments were performed on one donor and each experiment was performed in duplicate (N=8).

At the end of treatment duration with Rhodamine 123, the receptor fluid was directly analyzed in triplicate by a microplate spectrofluorometer SYNERGY 2 (Biotech) in order to measure the amount of Rhodamine 123 that reached the receptor fluid (absorption). Excitation and emission wavelengths were 485 and 590, respectively. Analysis was performed with Gen5 software.

The distribution of Rhodamine 123 in the skin was analyzed by epifluorescence microscopy. Skin samples were placed in a tissue holder and freeze-mounted in cryomount embedding medium. The frozen blocks were sectioned into slices 4-10 µm thick, perpendicular to the epidermal surface, in a cryomicrotome (Thermo Electron). The sections were collected on glass slides and dried. The cryosections were examined under an epifluoresent microscope with a TRITC filter (eclipse, 80i L; Nikon). The microscope, equipped with a digital camera (DS-5M-LI, Nikon) was used for image acquisition.

Figure 11:
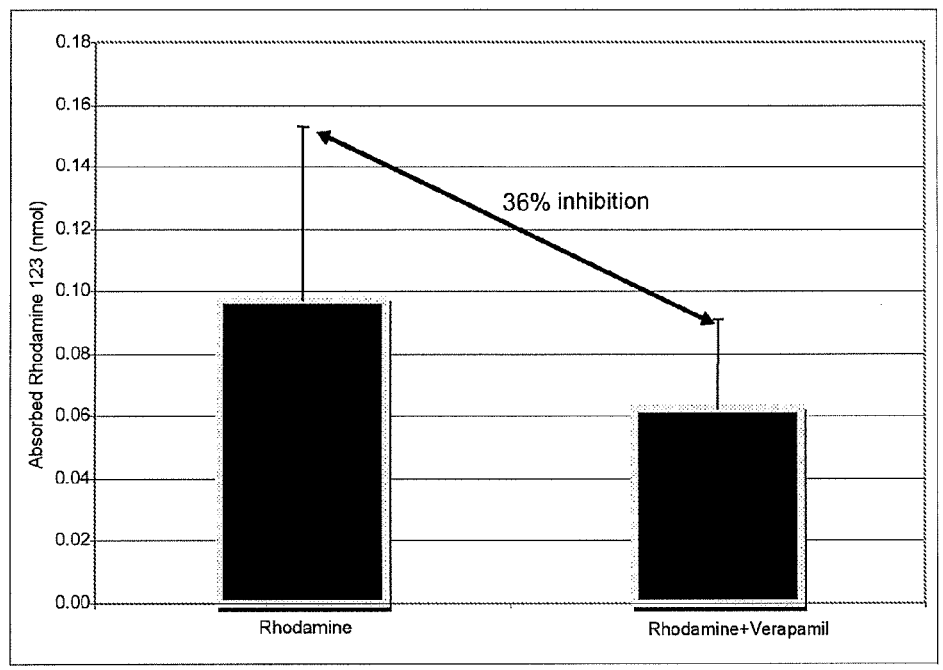
FIG. 11: Comparison of Rhodamine 123 skin absorption in human skin samples treated with Verapamil and Rhodamine 123 skin absorption in untreated human skin samples.

FIG. 11 (Effect of verapamil on Rhodamine 123 skin absorption in human skin samples) shows the effect of Verapamil on Rhodamine 123 skin absorption in human skin samples.

This result shows that in intact human skin samples, in vitro skin absorption of Rhodamine 123 was very low and represented about 0.4% of the applied dose. However, compared with Vinblastine skin absorption in intact skin samples, where skin absorption only represented 0.001% of the applied dose, Rhodamine 123 could be considered well absorbed.

Moreover, the result shows that in intact human skin samples, Rhodamine 123 skin absorption was significantly reduced by Verapamil treatment (t-test, $p<0.05$). Indeed, Rhodamine 123 absorption was reduced by 36% by topically applied Verapamil. As Verapamil is a known inhibitor of MDR1 transporter, this result suggests that MDR1 transporter is involved in the skin absorption of Rhodamine 123.

Figure 12:
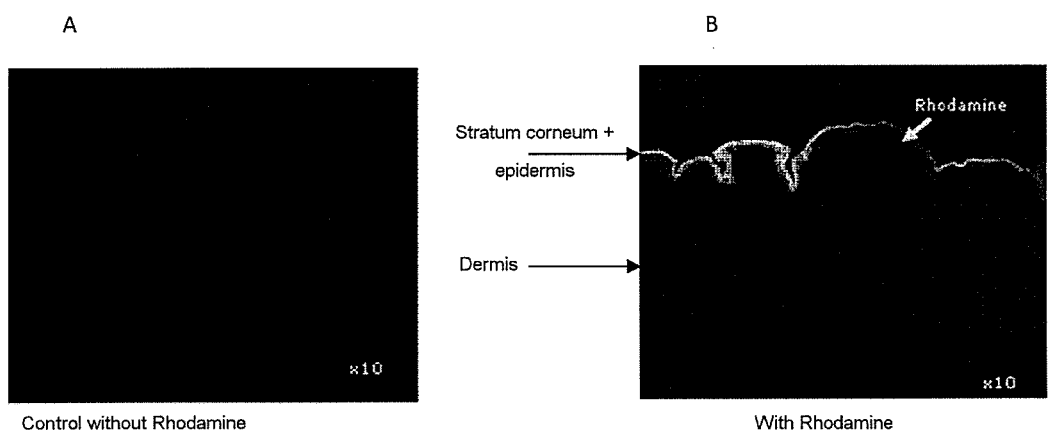
FIG. 12A: Skin section of control skin sample without any treatment showing the basal autofluorescence level.
FIG. 12B: Skin section of skin sample treated with Rhodamine 123 showing an increase of red fluorescence due to Rhodamine 123.

FIG. 12A skin section of control skin sample without any treatment (without Rhodamine) showing the basal autofluorescence level.

FIG. 12B skin section of skin sample treated with Rhodamine 123 showing an increase of red fluorescence due to Rhodamine 123.

These results show that Rhodamine 123 is mainly distributed in the uppermost layers of skin section, corresponding to epidermis and stratum corneum. Compared with control skin section, an increase of fluorescence in the dermis can also be observed indicating that Rhodamine 123 is also distributed in the dermis, but to a lesser extent. These results are in accordance with the results shown in FIG. 9, indicating that Rhodamine 123 was absorbed in the receptor fluid.

No difference in fluorescence intensity was observed in sections of skin samples treated with Verapamil (data not shown). This was probably due to the saturation of fluorescence signal observed in the uppermost layers of the skin samples.

The results presented in example 4 and in example 5 show that skin absorption of Vinblastine and Rhodamine 123, two substrates of the ABC transporters, was inhibited by Verapamil, an inhibitor of ABC transporter. This indicates that skin ABC transporters, mainly MDR1, are involved in the human cutaneous absorption and distribution of Vinblastine and Rhodamine 123.

EXAMPLE 5

Involvement of the ABC Transporters in the Absorption and Distribution of Leukotriene-C4 in Human Skin Samples The model substrate molecule leukotriene-C4 (LTC4) was used throughout this experiment. Leukotriene-C4 is known to be a physiological substrate of the MRP1 transporter.

The model inhibitory molecule MK571 was used throughout this experiment. MK571 is known to be a specific inhibitor of MRP1.

Tritium labeled LTC4 was used. The concentration of the LTC4 solution used was 68.5 nM (0.01 mCi/mL).

MK571 was prepared with a final concentration of 2 mM in water.

The vehicle used for treating the control skin samples consisted of 100% water. The skin samples were first treated with the MK571 inhibitor solution. To do this, 10 µL of MK571 solution were applied to the surface of skin samples, using a micropipette, corresponding to 10 µL/cm$^2$ of skin surface. The duration of the treatment with the inhibitor was 30 minutes.

In parallel, other skin samples (control samples) were treated with the constituted vehicle for the inhibitor used. To do this, 10 µL of water were applied to the surface of skin samples using a micropipette. The duration of the treatment with the vehicle was 30 minutes.

At the end of the period of treatment with the inhibitor, the skin samples, both the control samples and those treated with the inhibitor, were treated with the LTC4 solution. To do this, 10 µL of the 68.5 nM LTC4 solution were applied to the surface of each skin sample, corresponding to 10 µL/cm$^2$. The duration of the treatment with LTC4 was 6 hours.

At the end of the period of treatment with LTC4, the receptor fluid was analyzed by liquid scintillation counting for the purpose of measuring the amount of LTC4 which reached the receptor fluid (absorption).

The distribution of the LTC4 in the skin was analyzed by autoradiography. The experimental conditions are identical to those described previously for vinblastine.

The in vitro LTC4 skin absorption experiments were performed with fresh skin samples originating from three different donors. The experiments were performed in 6-well Transwell plates, with a 1 cm$^2$ area of treated skin and receptor fluid volumes of 1.5 mL. The treatment volume for the skin surface was 10 µL, corresponding to 0.69 µmol and 222 000 dpm. Three different experiments were performed with skin samples originating from three different donors. In each experiment, each condition was performed in triplicate (N=9 in total).

Figure 13:
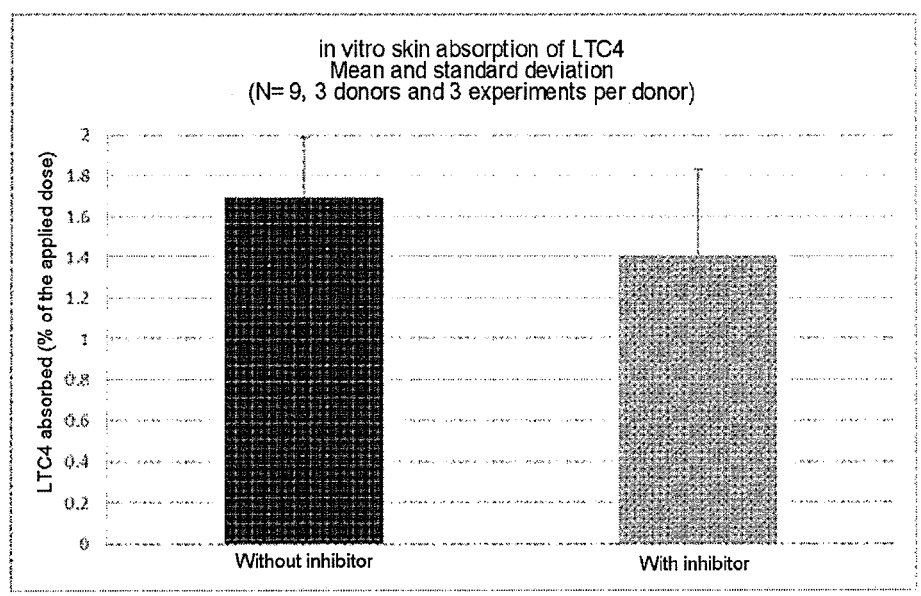
FIG. 13: Graphical representation of the effect of MK571 on the cutaneous absorption of LTC4 in human skin samples.

FIG. 13 (effect of MK571 on the cutaneous absorption of LTC4 in human skin samples) shows the effect of the inhibitor MK571 on the cutaneous absorption of LTC4 in human skin samples.

Figure 14:
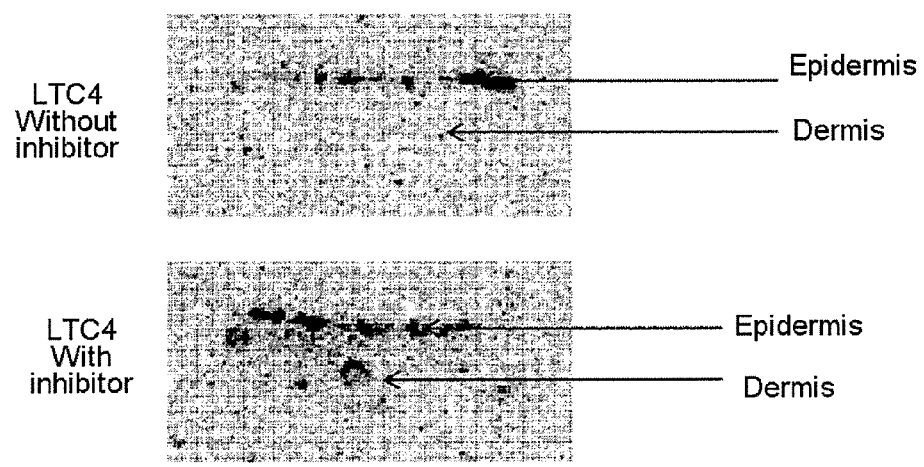
FIG. 14: Autoradiographs of skin sections showing the cutaneous distribution of LTC4 in skin samples with and without an inhibitor.

FIG. 14 (cutaneous distribution of LTC4 in skin samples analyzed by autoradiography of skin sections) shows the distribution of LTC4 in human skin with and without treatment with the MRP1 inhibitor MK571, analyzed by autoradiography.

This result shows that, in human skin samples, the in vitro cutaneous absorption of LTC4 after 6 hours of treatment was very low and represented about 1.7% of the applied dose. However, the cutaneous absorption of LTC4 is markedly higher than that of vinblastine and of rhodamine 123.

Furthermore, the result shows that, in the human skin samples, the cutaneous absorption of LTC4 was significantly reduced by a treatment with MK571 (t test, $p<0.05$). Specifically, the absorption of LTC4 was reduced by about 17% by topically applied MK571. Since MK571 is a specific inhibitor of the MRP1 transporter, this result suggests that the MRP1 transporter is involved in the cutaneous absorption of LTC4. The results of the LTC4 distribution analyzed by autoradiography show that, in the skin sections without treatment with the inhibitor, a radioactive signal related to LTC4 is observed in the uppermost part of the skin section corresponding to the epidermis. No signal was observed in the deeper layers. In the skin treated with the inhibitor, an appreciable increase in the intensity of the signal related to LTC4 was observed, especially in the deeper layers corresponding to the dermis. This indicates that the treatment of the skin with the inhibitor increases the penetration of LTC4 into the deeper layers of a skin sample. This result is in accordance with the result obtained in FIG. 13, showing that the treatment with the inhibitor appreciably reduces the amount of LTC4 absorbed in the receptor fluid.

All the results presented with the model molecules used as substrate and inhibitor of ABC transporters coupled with a human skin absorption system give strong evidence that the model presented in this work represents a sensitive, easy, and suitable tool to study the involvement of ABC transporters in the cutaneous absorption and distribution of topically applied drugs.

EXAMPLE 6

Immunolocalization of the MRP1 Transporter in Human Skin

A human skin sample (woman, 75 years old) originating from a face lift was used to study the localization of the MRP1 transporter by immunohistochemistry. Skin biopsies were included in cryomatrix (Shandon Thermo) and serial sections 4 µm thick were prepared using a cryomicrotome. The cryosections were recovered on glass slides (superfrost plus Thermo, 1.0 mm 25×75) and stored at −20° C. The MRPm6 (Tebu-bio) primary antibody raised against MRP1 was used. This is a monoclonal antibody produced from mice, with a concentration of 500 µg/mL. The primary antibody was used at a dilution of 1/100 (5 µg/mL). The secondary antibody supplied with the Ultra Vision LP kit, HRP/AEC (Labvision-Thermofisher) was used according to the supplier's instructions. Revelation was performed using the substrate aminoethyl carbazole (AEC), which made it possible to obtain a red precipitate at the reaction site.

Figure 15:
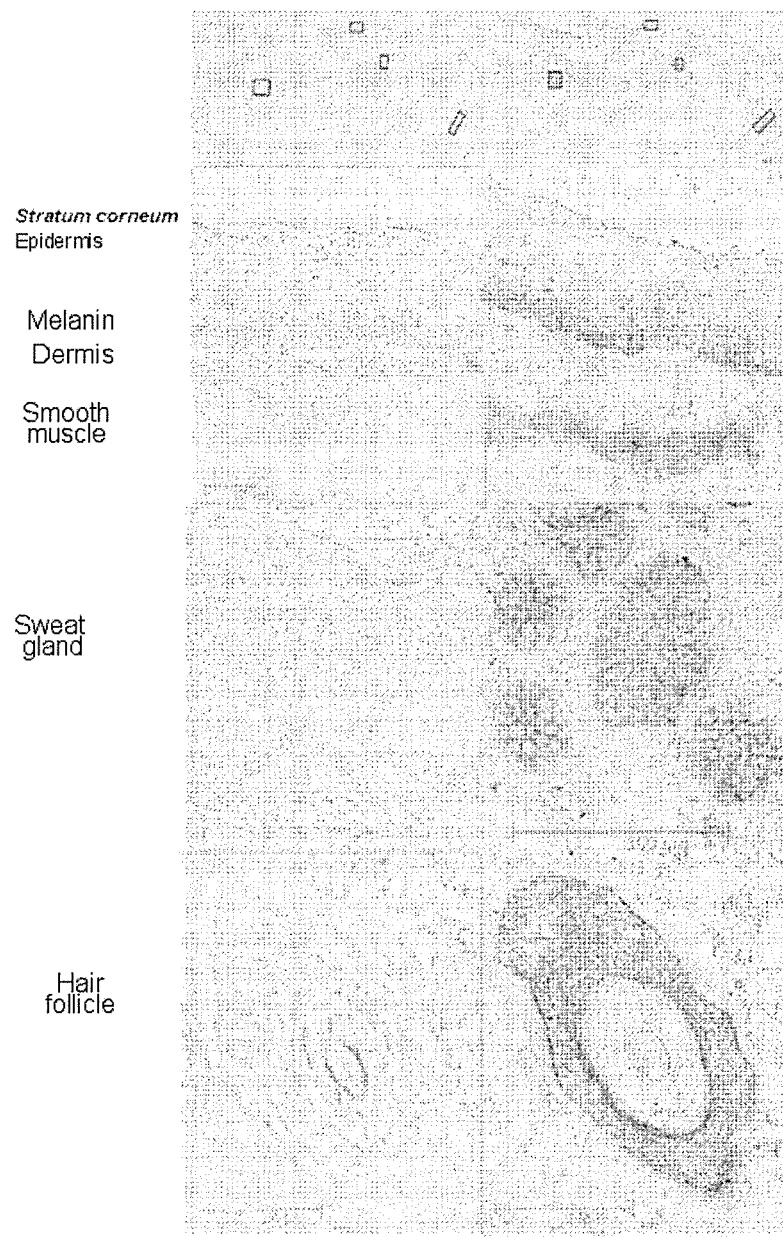
FIG. 15: Immunohistochemical images showing the localization of the MRP1 transporter in human skin.

FIG. 15 (localization of the MRP1 transporter in human skin by immunohistochemistry) shows the localization of the MRP1 transporter in human skin revealed by immunohistochemistry. The images corresponding to the negative controls (absence of primary antibody) are given on the left, and the images obtained after immunodetection of MRP1 are given on the right.

Immunohistochemistry revealed that the MRP1 transporter is indeed detected in the skin, and that it is mainly localized in the dermal appendages (sweat glands, hair follicles, smooth muscles). Similar results with MDR1 were recently reported (Skazik C. et al., 2011) showing a preferential localization in the dermis. The localization of MRP1 in the appendages, in particular in the hair follicles, argues in favor of a role of this MRP1 transporter in cutaneous absorption.

The invention claimed is:

1. A method for evaluating influence of ATP Binding Cassette (ABC) transporters on a penetration of a drug in human skin, the method comprising the steps of:
   (1) preparing ex vivo human skin samples, and maintaining skin samples in organoculture conditions;
   (2) contacting a first skin sample with a specific ABC transporter inhibitor solubilized in a vehicle in organoculture conditions;
   (3) contacting a second skin sample (control) with a vehicle in organoculture conditions;
   (4) contacting both control and ABC transporter inhibitor treated skin samples with a drug in organoculture conditions;
   (5) determining for each skin sample an amount of drug collected in a liquid receptor (absorption) after penetration through the skin;
   (6) determining for each skin sample an amount of drug located in the skin samples (distribution); and
   (7) comparing the level of uptake of the drug in the first skin sample (with inhibitor) with that of the control skin sample (without inhibitor).

2. The method according to claim 1, wherein the human skin samples are prepared ex vivo without subcutaneous fat.

3. The method according to claim 1, wherein the organoculture conditions are at about 37° C. during a period of time ranging from about 1 minute to about 72 hours.

4. The method according to claim 1, wherein the first skin sample is in contact with the ABC transporter inhibitor at about 37° C. during a period of time ranging from about 1 minute to about 1 hour.

5. The method according to claim 1, wherein the second skin sample is in contact with the vehicle at about 37° C. during a period of time ranging from about 1 minute to about 1 hour.

6. The method according to claim 1, wherein both the first (inhibitor) and the second (control) skin samples are in contact with the drug at about 37° C. and during a period of time ranging from about 1 hour to about 72 hours.

7. The method according to claim 1, wherein the drug used is selected for the treatment of skin diseases selected from the group consisting of inflammatory skin diseases, viral skin diseases, fungal skin diseases, bacterial skin diseases and cancerous skin diseases.

8. The method according to claim 6, wherein the period of time is about 16 hours.

\* \* \* \* \*